United States Patent
Koktava et al.

(10) Patent No.: US 9,779,505 B2
(45) Date of Patent: Oct. 3, 2017

(54) MEDICAL DATA PROCESSING APPARATUS AND METHOD

(71) Applicant: Toshiba Medical Systems Corporation, Otawara-shi (JP)

(72) Inventors: Rachel Louise Koktava, Edinburgh (GB); Paul Norman, Edinburgh (GB)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/501,486

(22) Filed: Sep. 30, 2014

(65) Prior Publication Data
US 2016/0092748 A1 Mar. 31, 2016

(51) Int. Cl.
*G06K 9/46* (2006.01)
*G06T 7/00* (2017.01)
*G06K 9/62* (2006.01)
*G06F 19/00* (2011.01)

(52) U.S. Cl.
CPC ............ *G06T 7/004* (2013.01); *G06F 19/321* (2013.01); *G06K 9/6201* (2013.01); *G06K 2209/05* (2013.01)

(58) Field of Classification Search
None
See application file for complete search history.

(56) References Cited

U.S. PATENT DOCUMENTS

| | | | | |
|---|---|---|---|---|
| 1,868,124 A | * | 7/1932 | Thomaschewski | C09B 1/42 552/256 |
| 4,120,160 A | * | 10/1978 | Davis | F01K 9/02 122/40 |
| 6,522,780 B1 | * | 2/2003 | Pass | G06F 17/30256 382/170 |
| 7,158,692 B2 | * | 1/2007 | Chalana | G06K 9/00 382/128 |
| 7,523,505 B2 | * | 4/2009 | Menschik | G06F 19/322 705/3 |
| 7,689,544 B2 | | 3/2010 | Koenig | |
| 2005/0207658 A1 | * | 9/2005 | Schofield | G06F 19/321 382/232 |

(Continued)

FOREIGN PATENT DOCUMENTS

| | | | | |
|---|---|---|---|---|
| CN | 1868124 A | * | 11/2006 | G06F 15/7867 |
| CN | 104007954 A | * | 8/2014 | G06F 15/7867 |

(Continued)

OTHER PUBLICATIONS

Mark O. Güld, et al., "Quality of DICOM header information for image categorization", Aachen University of Technology (RWTH), Aachen, Germany, (2002), 8 pages.

(Continued)

*Primary Examiner* — Tsung-Yin Tsai
(74) *Attorney, Agent, or Firm* — Oblon, McClelland, Maier & Neustadt, L.L.P.

(57) ABSTRACT

A medical image processing apparatus comprises a structure identification unit configured to automatically identify at least one anatomical structure of a medical image data set, and a metadata unit configured to validate or populate metadata associated with the medical image data set based on the identified at least one anatomical structure.

25 Claims, 4 Drawing Sheets

(56) References Cited

U.S. PATENT DOCUMENTS

| | | | | |
|---|---|---|---|---|
| 2006/0229911 A1* | 10/2006 | Gropper | ............... | G06F 19/321 705/2 |
| 2007/0064987 A1* | 3/2007 | Esham | ................... | A61B 6/481 382/128 |
| 2007/0118540 A1* | 5/2007 | Guo | ................. | G06F 17/30265 |
| 2007/0292012 A1* | 12/2007 | Brandon | ........... | G06F 17/30265 382/128 |
| 2008/0052112 A1* | 2/2008 | Zahlmann | ............. | G06F 19/321 705/2 |
| 2009/0010558 A1* | 1/2009 | Dekel | ............... | G06F 17/30247 382/248 |
| 2011/0110572 A1* | 5/2011 | Guehring | ............ | A61B 6/5258 382/131 |
| 2011/0188718 A1* | 8/2011 | Hill | ....................... | G06F 19/321 382/128 |
| 2012/0197619 A1* | 8/2012 | Namer Yelin | ...... | G06F 19/3437 703/11 |

FOREIGN PATENT DOCUMENTS

| | | | | |
|---|---|---|---|---|
| DE | 1868124 U | * | 2/1963 | |
| DE | 2947639 A1 | * | 9/1980 | ............. F16L 21/08 |
| DE | EP 0025926 A1 | * | 4/1981 | ............. C09B 1/42 |
| DE | EP 1868124 A2 | * | 12/2007 | ....... G06F 17/30265 |
| EP | 1 868 124 A2 | | 12/2007 | |
| GB | 243779 A | * | 12/1925 | ............. A61C 17/24 |
| GB | 2448811 A | * | 10/2008 | ........... G06F 19/321 |
| JP | 2013-45159 A | | 3/2013 | |
| SU | 498419 A1 | * | 1/1976 | |
| WO | WO 2012150514 A1 | * | 11/2012 | ........... G06F 19/321 |

OTHER PUBLICATIONS

DICOM standard, 2013 Public Comment Draft, part 03, ftp://medical.nema.org/MEDICAL/Dicom/2013/output/pdf/part03.pdf, (2013), 1260 pages.

DICOM standard, 2013 Public Comment Draft, part 06, ftp://medical.nema.org/Medical/Dicom/2013/output/pdf/part06.pdf, (2013), 194 pages.

DICOM standard, 2013 Public Comment Draft, part 10, ftp://medical.nema.org/MEDICAL/Dicom/2013/output/pdf/part10.pdf, (2013), 48 pages.

DICOM standard, 2013 Public Comment Draft, part 16, ftp://medical.nema.org/MEDICAL/Dicom/2013/output/pdf/part16.pdf, (2013), 1034 pages.

MINT Study Metadata Format Revision D, (May 6, 2011), 13 pages.

Antonio Criminisi, et al., "Regression Forests for Efficient Anatomy Detection and Localization in CT Studies", Medical Computer Vision, Recognition Techniques and Applications in Medical Imaging, MICCAI 2010 Workshop MCV, LNCS 6533, (2011), pp. 106-117.

Rene Donner, et al., "Global localization of 3D anatomical structures by pre-filtered Hough Forests and discrete optimization", Medical Image Analysis, vol. 17, No. 8, (2013), pp. 1304-1314.

David Liu, et al., "Anatomical Landmark Detection Using Nearest Neighbor Matching and Submodular Optimization", MICCAI 2012, Part III, LNCS 7512, (2012), pp. 393-401.

* cited by examiner

MEDICAL DATA PROCESSING APPARATUS AND METHOD

FIELD

The present invention relates to an apparatus and method for processing metadata associated with medical images, for example an apparatus and method for validating or populating DICOM data or other metadata.

BACKGROUND

Medical images are commonly stored using the DICOM standard. Metadata in the form of DICOM data elements can be used to categorize and semantically describe the medical images. The DICOM data elements or other metadata can be used to provide information such as the gender of a patient, a modality used to obtain a medical image, the anatomical area or feature scanned to obtain the medical image, and a range of other information relating, for example, to the patient, the scanner used to obtain medical image data, parameters of the scan itself, and date and time information.

The DICOM standard defines a range of attributes, which may be used to describe the properties of an information object. Each DICOM attribute is described by a pair of numbers (group number, data element number) which may be referred to as a tag. A list of certain DICOM attributes and tags is provided for example in the document Digital Imaging and Communications in Medicine (DICOM), Part 6: Data Dictionary, published by National Electrical Manufacturers Association, 1300 N.17$^{th}$ Street, Rosslyn, Va. 22209, USA.

The values of DICOM attributes for a particular information object may be encoded as DICOM data elements. Each data element may comprise the relevant tag and a value. In some circumstances, the DICOM attributes or data elements themselves may be referred to as tags.

Although a large number of attributes are available under the DICOM standard, it is often the case that many of the corresponding data elements for particular medical images are not populated with data. Furthermore, it has been found that data included in DICOM data elements that are populated for particular medical images is incorrect. That is often the case for anatomical data, for example data identifying particular anatomical features or regions that are the subject of a scan.

It is also the case for at least some known systems that for many of the attributes, particularly attributes relating to anatomical features such as Body Part Examined (0008, 0015) or Anatomic Structure (0008, 2208), a user may have a free choice of text or other data with which to populate data elements, rather than being constrained to a choice of standard terms. For example, although it is recommended in at least some systems to use an anatomical region code defined by the SNOMED lexicon to populate Anatomic Structure (0008, 2208) in the DICOM standard, that is not mandatory. Thus, even if an anatomical feature or region is identified correctly in one or more DICOM data elements for a particular set of medical image data, the same anatomical feature or region may be identified in data elements for another set of medical image data using different terms. Furthermore, typographical or other errors may occur when entering text or other data.

In addition, there can in practice be ambiguity or overlap between possible terms relating to anatomical features for use in populating data elements, or confusion on the part of an operator as to which terms should be used, particularly if a scan covers several body parts or regions, or overlaps more than one region (for example head and neck).

In some systems, certain DICOM data elements relating to anatomical features (for example Body Part Examined) may be set automatically based on a selection of imaging parameters by an operator, for example based on selection of an examination protocol. For instance, in some systems if an operator selects an examination protocol of a scanner suitable for scanning, say, a patient's head, imaging parameters are set by the scanner based on that selection, and a DICOM data element or data elements are automatically populated to indicate that the scan is of a head. However, in practice operators may select an examination protocol for one anatomical region (for example Head) even though the scan is of another anatomical region (for example, Abdomen) if they are aware that the scan parameters for the selected examination protocol are likely to produce a good image quality. Thus, DICOM data elements can be automatically populated with incorrect anatomical information in some cases.

There are significant potential issues if DICOM data elements are incorrectly assigned to sets of image data, particularly given the very large quantities of image data that are now stored in Picture Archiving and Communication Systems (PACS) and other large scale medical data storage systems. For example, patient image data may be incorrectly categorized, or patient image data may be lost or ignored. In some cases, incorrect DICOM data or other metadata may potentially lead to errors in diagnosis.

BRIEF DESCRIPTION OF THE DRAWINGS

Embodiments are now described, by way of non-limiting example, and are illustrated in the following figures, in which.

DETAILED DESCRIPTION

Certain embodiments provide a medical image data processing apparatus comprising a structure identification unit configured to automatically identify at least one anatomical structure of a medical image data set and a metadata unit configured to validate or populate metadata associated with the medical image data set based on the identified at least one anatomical structure.

Certain embodiments provide a medical image data processing method comprising automatically identifying at least one anatomical structure of a medical image data set, and validating or populating metadata associated with the medical image data set based on the identified at least one anatomical structure.

Figure 1:
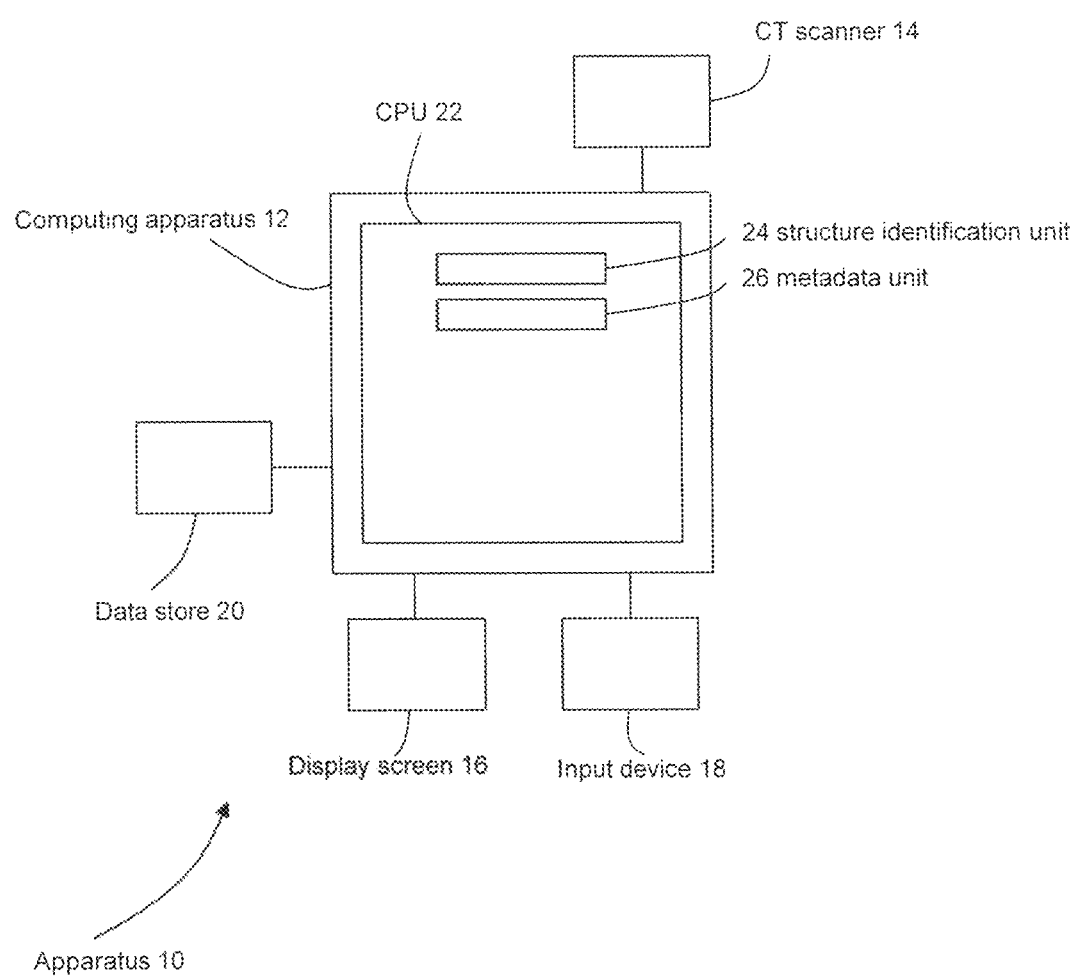
FIG. 1 is a schematic diagram of an image processing apparatus according to an embodiment.

An image data processing apparatus 10 according to an embodiment is illustrated schematically in FIG. 1.

The image data processing apparatus 10 comprises a computing apparatus 12, in this case a personal computer (PC) or workstation, that is connected to a CT scanner 14, a display screen 16 and an input device or devices 18, such as a computer keyboard and mouse. In the present embodiment, sets of image data 40 are obtained by the CT scanner 14 and stored in data store 20. In other embodiments, sets of image data may be loaded from a remote data store or other memory.

Computing apparatus 12 provides a processing resource for receiving and registering medical image data and virtual anatomy data. Computing apparatus 12 comprises a central processing unit (CPU) 22 that is operable to load and execute a variety of software modules or other software components that are configured to perform the method that is described below with reference to FIG. 3.

The computing apparatus 12 includes a structure identification unit 24 for identifying structures in medical image data and a metadata unit 26 for validating or populating metadata associated with the medical image data.

In the present embodiment, the structure identification unit 24 and metadata unit 26 are each implemented in computing apparatus 12 by means of a computer program having computer-readable instructions that are executable to perform the method of the embodiment. However, in other embodiments, the various units may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 1 for clarity.

Figure 2:
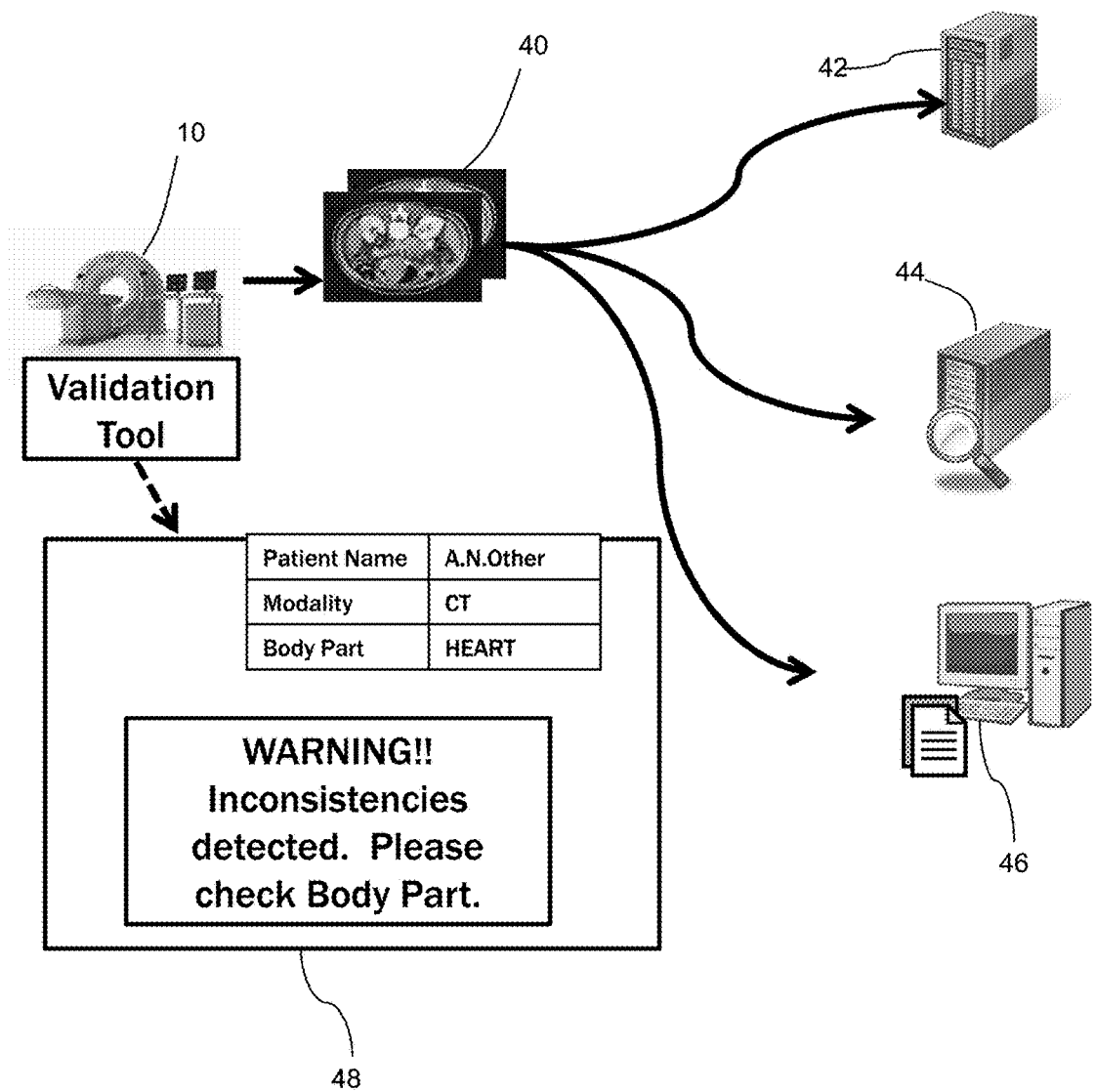
FIG. 2 is a schematic diagram of an image data acquisition system including the image processing apparatus of FIG. 1.

In the present embodiment, the image data processing apparatus 10 of FIG. 1 is integrated into an image data acquisition system as shown in FIG. 2. Image data processing apparatus 10 is configured to acquire medical image data using scanner 14, and to output medical image data sets 40 to various servers 42 or workstations 44, where the medical image data may be stored. Image data processing apparatus 10 is also configured to output medical image data sets 40 to user workstations 46, where a user (for example, a clinician) may view medical image data sets 40 along with other data, for example reports that are linked to the medical image data set, or patient files. In some embodiments, the image data processing apparatus 10 is configured to generate an error code if an inconsistency is found between image data 40 and its associated metadata, as is described in detail below with reference to the flowchart of FIG. 3.

In some embodiments, the image data processing apparatus 10 may comprise or form part of a Picture Archiving and Communication System (PACS) or Report System.

Figure 3:
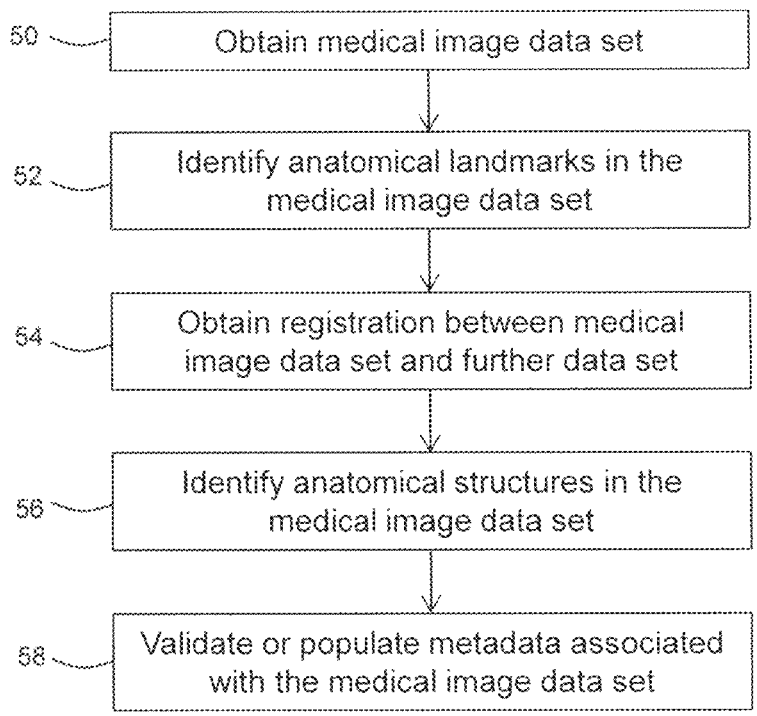
FIG. 3 is a flow chart illustrating in overview a method performed by the image processing apparatus of FIG. 1.

The apparatus of FIG. 1 is configured to perform a series of stages as illustrated in overview in the flow chart of FIG. 3.

At stage 50 of FIG. 3, the structure identification unit 24 receives from data store 20 a volumetric medical image data set 40 obtained from a CT scan of a patient or other subject. In the present embodiment, the image data set 40 and associated metadata form part of a DICOM (Digital Imaging and Communications in Medicine) study. The metadata comprises DICOM data elements. The volumetric medical image data set 40 may comprise multiple two-dimensional DICOM image files (which together form a volume) and the majority of the DICOM metadata may be replicated in each of the two-dimensional DICOM image files.

In the present embodiment, when the CT scan is taken, a set of metadata is automatically generated which is associated with the image data set. When an operator selects an examination protocol, for example, an examination protocol suitable for scanning a patient's head, a DICOM data element or data elements are automatically populated to indicate that the scan is of a head. The CT operator may also manually add entries into DICOM data elements, using for example a free-text field to enter anatomical structures being scanned. In further embodiments, the metadata may be of any format (which may or may not be DICOM) and may be generated automatically, manually, or by a combination of automatic and manual processes.

It has been found that DICOM data, particularly DICOM data manually added by an operator, may often be missing, incomplete, or of a non-standard form.

In the present embodiment, the image data set 40 is obtained from a CT scan taken using CT scanner 14, which is connected to image data processing apparatus 10. In alternative embodiments, the CT scan is taken using any CT scanner. In other embodiments, the image data set 40 comprises data obtained from any radiological scanner that produces radiological data in any modality, for example CT, MRI, ultrasound, PET or SPECT. The image data set 40 may comprise volumetric or two-dimensional image data.

Although in the present embodiment, the structure identification unit 24 receives the image data set 40 from data store 20, in other embodiments, the structure identification unit 24 receives the image data set 40 from a remote data store, for example from a server 42 which may form part of a Picture Archiving and Communication System (PACS). In further embodiments, the structure identification unit 24 receives the image data set 40 directly from the scanner 14.

At stage 52, the structure identification unit 24 uses a landmark location algorithm to automatically identify known anatomical landmarks in the image data set 40 and to determine the location of each anatomical landmark in the coordinate system of the image data set 40.

An anatomical landmark is usually a well-defined point in an anatomy. In the present embodiment, the anatomy is a human anatomy but in other embodiments the anatomy may be any animal anatomy. Anatomical landmarks may be defined anatomically, in relation to anatomical structure such as bones, vessels or organs. Examples of anatomical landmarks include the center of the right eye and the apex of the right lung. The anatomical definition of a landmark may be used to locate that landmark in many different medical imaging data sets, or in virtual anatomies. For example, a landmark may be defined at the center of the right eye. The center of the right eye may be located in any medical image data set or virtual anatomy in which the center of the right eye is present, by any manual or automatic method that can locate that point in the anatomy.

The present embodiment uses a set of 127 known anatomical landmarks (anatomical landmarks for which anatomical definitions have been pre-determined). In other embodiments, a different set of anatomical landmarks may be used. Different sets of landmarks may comprise different landmarks (for example, the center of the right eye may be included as a landmark in one set of anatomical landmarks but not included as a landmark in another set of anatomical landmarks) or may comprise different numbers of landmarks (for example, 100 rather than 127).

In the present embodiment, for each of the set of 127 anatomical landmarks, the structure identification unit 24 determines whether that landmark is present in the image data set 40 by using a classification method to determine whether the relevant anatomy is present. For example, for the anatomical landmark defined at the center of the right eye, the structure identification unit 24 determines whether the center of the right eye is present in the image data set 40 by using a trained classifier. If the relevant anatomy is not present, the structure identification unit 24 returns no coordinates for the anatomical landmark in the image data set 40.

If the relevant anatomy is present, the structure identification unit 24 determines the location of the landmark in the image data set 40 as a set of coordinates in the coordinate space of the image data set 40. For example, the structure identification unit 24 determines the position of the center of the right eye as a point in the image data set 40, and returns the coordinates of that position. The determined location of the landmark is specific to the particular image data set 40. A similar process of detection and location is performed for each of the set of 127 known anatomical landmarks.

In the present embodiment, the structure identification unit 24 detects the anatomical landmarks automatically using classifiers. Detection and localization of pre-defined anatomical landmarks in medical image data is performed by a classification forest which uses simple image features. Detection results are refined with reference to the spatial relationships between the landmarks.

In other embodiments, any other suitable method of landmark detection may be used. Methods of landmark detection may be as described in, for example, Criminisi, Shotton, Robertson and Konukoglu (2011), 'Regression forests for efficient anatomy detection and localization in CT studies', *Medical Computer Vision. Recognition Techniques and Applications in Medical Imaging,* 106-117; Donner, Menze, Bichof and Langs (2013), 'Global localization of 3D anatomical structures by pre-filtered Hough forests and discrete optimization', *Medical Image Analysis,* 17(8), 1304-1314, doi:10.1016/j.media.2013.02.004; or Liu and Zhou, 'Anatomical landmark detection using nearest neighbor matching and submodular optimization', *Medical image computing and computer-assisted intervention (MICCAI),* 7512, 393-401.

Figure 4:
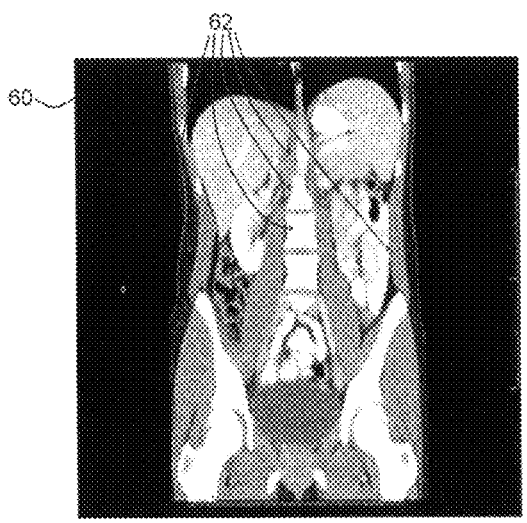
FIG. 4 is an image obtained from a medical image data set and including indicators of landmarks detected during performance of the method of FIG. 3.

FIG. 4 shows a medical image 60 derived from image data set 40. Several landmarks 62 are indicated on medical image 60. In alternative embodiments, alternative anatomical identifiers may be used instead of landmarks.

Figure 5:
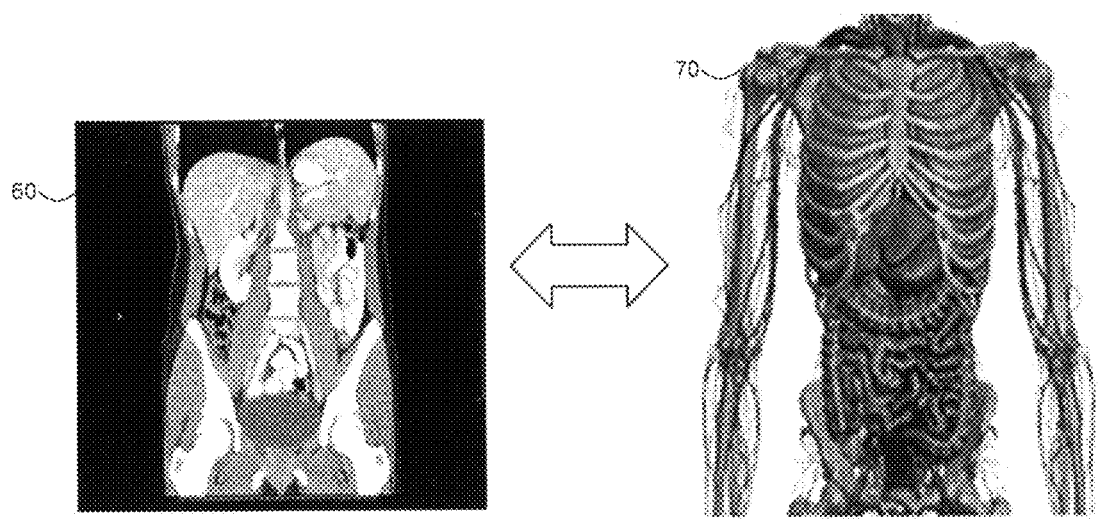
FIG. 5 shows the image of FIG. 4 and an image obtained from a virtual anatomy data set.

At stage 54, the structure identification unit 24 uses the detected landmarks to register the patient data set with a virtual anatomy which contains the position and shape of anatomical structures making up the human anatomy, as described below. FIG. 5 shows a medical image 60 and corresponding virtual anatomy image 70.

The structure identification unit 24 receives a virtual anatomy data set and an associated set of virtual anatomy landmark locations from the data store 20, or from an alternative data store. In the present embodiment, the virtual anatomy data set is a mesh-based virtual anatomy. The virtual anatomy data set comprises coordinates of each mesh vertex for each mesh in the virtual anatomy data set, and edges connecting the mesh vertices. In other embodiments any virtual anatomy may be used. The virtual anatomy may be mesh-based or volumetric.

The associated virtual anatomy landmark locations are the locations of landmarks within the virtual anatomy data set. In the present embodiment, an expert has manually identified and determined the positions of each of the anatomical landmarks in the virtual anatomy data set, which have then been stored in data store 20 prior to the process of FIG. 3. In other embodiments, the expert determination of the landmark positions may occur at any time. The landmarks in the virtual anatomy data set may be described as being ground truthed.

While in the present embodiment, the virtual anatomy data set and the associated set of virtual anatomy landmark locations are separate data sets, in other embodiments the virtual anatomy data set may comprise the locations of the landmarks within the virtual anatomy.

In the present embodiment, the virtual anatomy data set represents an entire human body. Therefore, each of the 127 landmarks that is anatomically defined is present in the virtual anatomy data set. In alternative embodiments, fewer landmarks may be present in the virtual anatomy data set than are anatomically defined for the generic human body (for example, in one embodiment 127 landmarks are defined anatomically on the human body, of which 90 are present in the virtual anatomy data).

The structure identification unit 24 establishes a correspondence between the location of each landmark in the image data set 40 and the location of its corresponding landmark in the virtual anatomy data set. For example, in an embodiment, each of the image data set 40 and the virtual anatomy data set includes the landmark at the inferior tip of the sternum. The structure identification unit 24 associates the location of the landmark at the inferior tip of the sternum in the image data set 40 with the location of the landmark at the inferior tip of the sternum in the virtual image data set.

It is to be expected that the location of each landmark will be different in the image data set coordinate space than in the virtual anatomy coordinate space, since each anatomical structure of the patient may differ from that of the virtual anatomy in size, shape and location, and the patient may be positioned differently in space from the virtual anatomy.

The structure identification unit 24 performs a registration of the image data set 40 and the virtual anatomy data set using the relationship between corresponding landmark locations.

The location of each anatomical landmark that is present in the image data set 40 has a corresponding location for that anatomical landmark in the virtual anatomy data set. The aim of the registration process is to determine a transformation between the image data set coordinate space and the virtual anatomy coordinate space and optimize that transformation. The transformation is considered to be optimized when, if the image data set 40 were transformed into the virtual anatomy coordinate space using the optimized transformation, the location of each anatomical landmark in the transformed image data set would coincide, as nearly as possible, with the location of the corresponding anatomical landmark in the virtual anatomy data set.

In alternative embodiments, a transformation from the virtual anatomy coordinate system to the image data set coordinate system is determined, rather than a transformation from the image data set coordinate system to the virtual anatomy coordinate system.

In the present embodiment, the transformation is determined and optimized based on the locations of anatomical landmarks in the medical image data and the locations of corresponding anatomical landmarks in the virtual anatomy data. Each landmark location may comprise a set of coordinates, and in the present embodiment only the landmark locations are used in the determining of the transformation. The information used to determine the transformation does not comprise, for example, intensity information associated with the anatomical landmarks.

The transformation defines a mapping from coordinates in the coordinate space of the image data set 40 to coordinates in the coordinate space of the virtual anatomy data set. In the present embodiment, the transformation is defined for all voxels in the image data set 40.

A distance measure may be calculated for the transformation, which for example comprises a mean Euclidean distance between each landmark location in the transformed image data set and its corresponding landmark location in the virtual anatomy data set. The structure identification unit 24 may determine the optimum transformation by minimizing the mean Euclidean distance between the landmarks in the transformed image data set and corresponding landmarks in the virtual anatomy data set. In other embodiments, any distance measure or other suitable metric may be used.

In the present embodiment, the transformation is optimized using a gradient descent method. In other embodiments, any suitable optimization method may be used.

The transformation may be a rigid transformation comprising rotation, translation and scaling. In other embodiments, the transformation is an affine transformation comprising rotation, translation, scaling and shearing, or a non-rigid transformation comprising deformation, which may include local deformation.

Although in the present embodiment the registration of the image data set 40 and the virtual anatomy data set comprises determining a transformation based on the locations of anatomical landmarks in the medical image data and the locations of corresponding anatomical landmarks in the virtual anatomy data, in other embodiments any suitable registration method may be used.

At stage 56, the structure identification unit 24 uses the registration between the virtual anatomy data set and the image data set 40 to identify anatomical structures in the image data set, for example based on a bounding volume or outer boundary of the image data set.

The bounding volume of the image data set 40 may be a volume of coordinate space that is occupied by the image data set 40, for example that is bounded by an outer boundary of the image data set. The bounding volume of the image data set 40 may be referred to as the image bounding volume. The image bounding volume may represent the overall extent of the scan. The image bounding volume is initially defined in the coordinate space of the image data set 40.

The structure identification unit 24 uses the determined transformation that defines the mapping from the image data set 40 to the virtual anatomy data set to calculate the bounding volume of the image data set 40 in the coordinate space of the virtual anatomy data set.

In the present embodiment, the virtual anatomy data set contains bounding boxes which define the approximate extent of the anatomical structures that it contains. While in the present embodiment, the bounding boxes are part of the virtual anatomy data set, in other embodiments the bounding boxes may form a separate data set. In further embodiments, the extent of anatomical structures may be defined through techniques such as, for example, axis aligned bounding boxes, non-axis aligned bounding boxes, composite volumes or meshes.

For each of the anatomical structures in the virtual anatomy data set, the structure identification unit 24 performs an intersection test between the bounding box of the anatomical structure and the image bounding volume that has been calculated in the virtual anatomy space.

If the bounding box of an anatomical structure intersects with the image bounding volume, then that anatomical structure is identified as being represented in the image data set 40.

In alternative embodiments, any method of identifying anatomical structures may be used. In some embodiments, a probability of identification is calculated when an anatomical structure is identified.

The structure identification unit 24 forms a list of anatomical structures that are identified as being represented in the image data set 40. Each anatomical structure that is identified as being represented in the image data set 40 is added to the list of anatomical structures.

Although in the current embodiment, anatomical structures are identified and added to a list of anatomical structures, in other embodiments anatomical regions may be determined. Any reference to an anatomical structure below may also refer to an anatomical region.

In some embodiments, a probability threshold is used to determine which of the anatomical structures to add to the list of anatomical structures that have been identified in the image data set 40. For example, in some embodiments, only anatomical structures with at least a 90% probability of identification are added to the list of anatomical structures.

Although in the present embodiment, an anatomical structure is identified as being represented in the image data set if its bounding box intersects with the image bounding volume in virtual anatomy space, in other embodiments, an anatomical structure is identified as being represented in the image data set only if its bounding box is fully contained within the image bounding volume. In such embodiments, an anatomical structure is not identified as being represented in the image data set if only part of its bounding box is within the image bounding volume, that is, if only part of the anatomical structure is represented in the image data set.

At stage 58, the metadata unit 26 receives the set of metadata that is associated with the image data set 40. In the present embodiment, the set of metadata comprises a set of DICOM data elements, including Body Part Examined (0008, 0015). The metadata unit 26 receives from the structure identification unit 24 the list of anatomical structures that was generated in stage 56.

The metadata unit 26 compares the list of anatomical structures to the contents of the Body Part Examined data element in the metadata associated with the image data set 40. The metadata unit 26 performs a consistency test in which the metadata unit 26 determines whether the contents of the Body Part Examined data element are consistent with the anatomical structures in the list of anatomical structures. Although in the present embodiment, the Body Part Examined data element is used, in other embodiments, other DICOM data elements or non-DICOM metadata may be used.

The metadata unit 26 uses an anatomical ontology in determining consistency between the contents of the Body Part Examined data element and the list of anatomical structures. The anatomical ontology may define relationships between anatomical features. For example, the anatomical ontology may define which structures are part of other structures. The anatomical ontology may define, for example, that the ears, eyes and mouth are part of the head, and the left thigh is part of the left leg. The anatomical ontology may also define which structures are connected to other structures. The anatomical ontology may include alternative terms for body parts, which may include foreign language terms or common misspellings. In alternative embodiments, no anatomical ontology is used.

In the present embodiment, each anatomical structure for which a bounding box is present in the virtual anatomy has an associated anatomical region term as defined by the SNOMED lexicon. The list of anatomical structures is a list of such anatomical region terms. In other embodiments, different names for the anatomical structures may be used.

In the present embodiment, the contents of the Body Part Examined data element are found to be consistent with the list of anatomical structures if each of the structures mentioned in the Body Part Examined data element is consistent with a respective structure in the list of anatomical structures.

If a first structure is the same as a second structure then the first structure may be considered to be consistent with a second structure. This includes cases in which a different name is used for the same structure, for example the first structure is named "leg" and the second structure is named "jambe". The first structure is also consistent with the second structure if the first structure is a part of the second structure (for example, the first structure is knee and the second structure is leg). The first structure is also consistent with the second structure if the second structure is a part of the first structure (for example, the first structure is leg and the second structure is knee). In some scans, the DICOM file may specify a small-scale feature while the landmark method identifies a larger structure or vice versa.

In further embodiments, an identified anatomical structure or region of the image data set 40 is consistent with an anatomical structure or region in the metadata if the identified anatomical structure or region in the image data and the anatomical structure or region in the metadata are expected to be present in substantially the same region of a human or animal body.

If each structure mentioned in the Body Part Examined data element is consistent with at least one structure in the list of anatomical structures, and there is no structure in the Body Part Examined data element that is not consistent with at least one structure in the list of anatomical structures, then the metadata unit 26 determines that the image data set 40 and associated metadata have passed a consistency test.

In the present embodiment, if the consistency test is passed, then the metadata unit 26 takes no further action and the process of FIG. 3 is complete. In alternative embodiments, if the consistency test is passed, then the metadata unit 26 may display a message on a screen (for example, 'data check complete'), or provide any other indication that the process is finished.

If the consistency test is failed, then the metadata unit 26 returns an error code (or, equivalently, raises an exception if the programming language supports exception handling). Such an error code (or exception) may be used to inform other software components that an inconsistency has occurred.

In the present embodiment, the error code results in the metadata unit 26 generating a warning signal causing display of a warning message 48. In the present embodiment, the warning message is a text display on display screen 16 comprising the patient's name, the modality of the scan, details of the body part or body parts included in the DICOM data elements, and a message that reads 'WARNING!! Inconsistencies detected. Please check Body Part.' In other embodiments, any suitable warning signal may be used, for example a warning signal that comprises or causes output of any desired text display, a visual indication (for example, filename turns red), or an audible indication (for example, a beep). In further embodiments, a warning message is sent to a user, for example by sending an email.

In alternative embodiments, the error code is passed to any other software component or unit that may make take an action based on the error code (or exception). For example, the error code may be used in verification of data set integrity, or in the validation of start-up or boundary conditions for algorithms.

In the present embodiment, the consistency test is failed if there is a structure listed in the DICOM data element that is not consistent with any structure in the list of anatomical structures. For example, the DICOM data element specifies knee, but no knee, structure containing a knee (for example, leg), or structure that is part of a knee (for example, kneecap) is present in the list of anatomical structures that was obtained from the image data. The consistency test may also be failed if the DICOM data element is empty. The consistency test may also be failed if the DICOM data element contains a term or terms that cannot be identified.

It may be seen that in the present embodiment, it is necessary that every structure in the DICOM data element is consistent with a respective structure in the list of anatomical structures, but the reverse does not apply. The consistency test may be passed when there are structures in the list of anatomical structures that are not consistent with any structures in the DICOM data element (as long as there are no structures in the DICOM data element that are not consistent with structures in the list of anatomical structures).

In fact, it may be expected that in many cases the list of anatomical structures will contain more structures than those specified than the DICOM data element. This is because the scan may often image a wider area than that required by the clinician. For example, a scan that is performed to image the heart (with a DICOM data element specifying heart only) may also include at least part of the lungs, ribs, aorta, vertebrae, or other nearby body parts.

In the present embodiment, the list of anatomical structures includes all structures for which the bounding box of the structure intersects the image bounding volume (in the virtual anatomy space). Therefore even structures for which only a part of the structure is included in the image will be specified in the list of anatomical structures.

If the consistency test is failed, an error code or exception may be generated as detailed above. A warning message may be displayed on display screen 16 or an alternative warning indication may be given. The warning message may prompt the clinician or other operator to examine the image data (for example, by requesting the display of an image derived from the image data set 40) to check whether there is a discrepancy between the body part or body parts present in the image data and the body part or body parts specified in the DICOM data element.

In the present embodiment, only a text warning message 48 is displayed. In other embodiments, an image derived from image data set 40 or the list of anatomical structures obtained at stage 58 may be automatically displayed at the same time as the text warning message 48. In some embodiments, a table is displayed which lists structures determined in the image and structures specified in the DICOM data element.

In the present embodiment, no action is required from the user in response to the warning message 48. In other embodiments, the user is required to indicate that they have read the warning message 48, for example by clicking on a button. In further embodiments, the user is required to view an image derived from the image data set 40 and to select one input (for example, click on a button) if the DICOM data elements are correct and a different input (for example, click on a different button) if the DICOM data elements are incorrect. Such embodiments may allow for the user to override the results of the consistency test in cases where the metadata unit 26 has incorrectly determined that the consistency test has been failed (for example, cases in which a foreign language term has been used that is not known in the anatomical ontology, and the foreign language term correctly describes a structure present in the image data set 40). Alternatively or additionally, the user may make manual entries or changes to DICOM data elements, or other data, in response to the warning message or as part of any other exception handling procedure.

In further embodiments, an interface is displayed that allows the user to make a note on the patient's file. The user may make a note of whether the user believes the DICOM data elements to be correct or not. In some embodiments, an interface is displayed that allows the user to add data, for example a data file, that is associated with the image data set. For example, the user may add a note associated with the image data set 40 to say that the DICOM data elements have been checked and confirmed, or that they have been checked or found to be incorrect. If incorrect, the user may add a note of the correct anatomical structures. The interface may allow the user to create a note or other file using the identified anatomical structures. In most embodiments, the original DICOM data is preserved even if it is found to be incorrect.

The process of FIG. 3, or similar embodiments, may be used in a number of medical contexts.

In some embodiments, the process of FIG. 3 is used for initial error checking. In one embodiment, the process of FIG. 3 is used when image data is taken at the CT scanner 14. A user inputs scan parameters into the CT scanner 14, for example by using a keyboard or choosing from drop-down menus. Amongst the parameters entered by the user is a free-text field for body part examined. The user then starts the CT scan. An image data set 40 is acquired. The image data set 40 has an associated set of metadata. In the set of metadata, the text entered by the user into the field for body part examined is added to the DICOM data element Body Part Examined.

Prior to saving the image data set 40 and associated metadata in a medical information system (for example, a PACS system), the image data set 40 and associated metadata is passed to computing apparatus 12, which comprises the structure identification unit 24 and metadata unit 26. In some embodiments, the computing apparatus 12 is part of a PACS or Report system (which may be the same system into which the image data set 40 and associated metadata is saved). In alternative embodiments, the structure identification unit 24 and metadata unit 26 are part of the CT scanner 14 or an associated workstation.

An immediate, or near-immediate, analysis of the image data set 40 is performed using the process of FIG. 3. A list of anatomical structures is generated by the structure identification unit 24 from the image data set 40 obtained from the CT scan. The metadata unit 26 then validates the relevant DICOM data elements (in this embodiment, Body Part Examined) against the list of anatomical structures, to determine whether the structures in the Body Part Examined data element (which in this embodiment are terms entered by the user) have been identified as being present in the image data set 40.

In this embodiment, if the consistency test is passed, no indication is given to the user. The image data set 40 and associated metadata are stored in the medical information system (for example, PACS). In an alternative embodiment, the metadata unit 26 displays a message to the user to indicate that the consistency test has been passed and/or that the image data set 40 and associated metadata have been successfully saved.

In this embodiment, if the consistency test is failed, an error code is generated or an exception is raised. The user may be alerted by a warning message. The user may be alerted before saving the scan data so that the user has an opportunity to correct any mistakes made.

On receiving the warning message, the user may choose to change their input into the text box for body part examined. The user may enter different text into the text box to that entered originally. In some similar embodiments, a further interface is displayed with the warning message (for example, a pop-up screen) which solicits text from the user. In such embodiments, the user may enter the new text into a different text box from that in which the original text was entered.

In this embodiment, if the user provides new text input for the body part examined, the text in Body Part Examined data element is updated to include the new text. The DICOM study as saved includes the new text instead of the original text. In some embodiments, both sets of text may be saved. For example, the DICOM file may include the new text, but the old text may be saved in an associated file with an indication that it is an obsolete version.

In the present embodiment, if the consistency test is failed, the user may not proceed to save the data until the user indicates that they have seen the warning message. The user may determine that their original input is correct, in which case they may override the warning message. The original text entered by the user is saved to the DICOM file. In other embodiments, no user override is available, and the user is required to change the text in the text box before the image data set 40 and associated metadata are saved.

In some embodiments, if the user changes the text in the text box, the process of FIG. 3 may be repeated to test the new text for consistency. Once text has been entered that is consistent with the anatomical structures identified by the structure identification unit, the image data set 40 and associated metadata are saved.

The process of FIG. 3 may be performed when an image data set 40 and associated metadata is added to a PACS or to another storage system. The process of FIG. 3 may be performed by the PACS or Report system, or other medical information system, in some embodiments. The process of FIG. 3 may or may not have been performed on acquisition of the image data set 40 as described above.

On being added to a PACS or other storage system, the process of FIG. 3 is performed on the image data set 40 and associated metadata. If discrepancies between the image data set 40 and associated metadata are identified an error code is generated or an exception is raised.

In some embodiments, a report is generated describing any inconsistencies found. For example, in an embodiment in which a large number of image data sets 40 are being added to a PACS as part of one batch of data, a report may be generated that identifies which of the image data sets 40 have an inconsistency between the structures indicated in the Body Part Examined data element and the structures identified in the image data set 40. In some embodiments, a daily, weekly or monthly report is generated which identifies all image data sets 40 added to the PACS that day, week or month in which inconsistencies were found.

In some embodiments, a flag is added to each file for which an inconsistency is found. Adding a flag may allow such files can be easily identified on searching the system. Adding a flag may allow a notification to be provided to a user when that user is about to open a file for which an inconsistency has been identified.

In some embodiments, the process of FIG. 3 is performed on an image data set 40 when a user selects or opens an image data set 40. In some cases, the user can request that the process of FIG. 3 is performed on an image data set 40, for example by clicking a button or typing in a text command.

The process of FIG. 3 may be performed on stored data, for example as part of a data clean-up project. For example, the process of FIG. 3 may be performed on each data set in a stored archive of data sets. For each of the data sets, if an inconsistency is found, an error code is generated or an exception is raised. A report may be generated which indicates which image data sets 40 in the stored archive have an inconsistency between structures in the Body Part Examined data element and structures represented in the image data set 40 (as determined using the process of FIG. 3)

The process of FIG. 3 may be performed on multiple image data sets 40 pertaining to the same patient. In some embodiments, the process of FIG. 3 may be performed on multiple data sets that were taken on the same scanner or scan operator. For example, if it has been determined that a particular piece of scan equipment or scan operator has a history of not populating the DICOM data elements correctly, image data sets 40 from that equipment or operator may be reviewed using the process of FIG. 3.

As already described, an inconsistency between the image data set 40 and the metadata may result in, for example, an error code, an exception, a warning message, a report or a flag. In alternative embodiments, if an inconsistency is found between the image data set 40 and the metadata, the information in the DICOM data element is replaced with the structures in the anatomical list. However, such embodiments may have limited application in a hospital setting, for which it may be appropriate or required to retain the original data. In such settings, an additional file may be added to the image data set 40, or a note may be made on the patient's record.

In further embodiments, the anatomical structures identified at stage 56 may be used at stage 58 to populate metadata associated with the image data set 40, for example to populate one or more DICOM data element. In some embodiments, image data sets 40 are identified for which a relevant DICOM data element, for example the Body Part Examined tag, is unpopulated. The metadata unit 26 uses the identified anatomical structures to populate Body Part Examined. In some embodiments, the metadata unit 26 requests user confirmation before the data element is populated.

The process of FIG. 3 may be used to automatically populate the DICOM data element when the patient is scanned. For example, if the probability of identification of an anatomical structure meets a defined threshold (for example, 99.9%) then the anatomical structure is added to the DICOM data element. However, in many clinical procedures, the process of FIG. 3 may be used only for validation of data elements and not for population of data elements. Some clinical procedures may require any automatically populated metadata to be reviewed and accepted by a user.

The process of FIG. 3 may be used to automatically identify anatomical structures in the image data set 40 when the patient is scanned. The structure identification unit 24 determines a list of anatomical structures in the image data set 40. The structure identification unit 24 then displays the list of anatomical structures to the user, for example as a drop-down list. The user selects the anatomical structures in the list that the user wishes to add to the DICOM data element. The metadata unit 26 then adds the selected anatomical structures to the DICOM data element.

Although the process of FIG. 3 is described above with reference to the Body Part Examined DICOM attribute, the process of FIG. 3 may also be used to validate or populate data elements corresponding to other DICOM attributes, for example Anatomic Structure (0008, 2208) or Anatomic Region Sequence (0008, 2218).

In some embodiments, the method may be used to validate or populate data elements corresponding to other Information Object Definitions, for example in General Anatomy macros such as the General Anatomy Mandatory Macro (DICOM PS 3.3 Table 10-5) or the General Anatomy Optional Macro (DICOM PS 3.3 Table 10-7).

In further embodiments, the structure identification unit 24 may be configured to determine at least one property of the patient using the identified anatomical structures. For example, the structure identification unit 24 may use the identified anatomical structures to determine the orientation of the patient in the scan. The structure identification unit 24 may identify whether the patient has been scanned head first or feet first, for example by using the relative positions of the identified anatomical structures. In other embodiments, the structure identification unit determines a zoom or magnification level, or a size of the scan area or volume.

In other embodiments, the property may be the sex of the patient. The structure identification unit 24 may determine the sex of the patient by detecting appropriate anatomical structures in the image data set 40. In other embodiments, the property may be the age of the patient. In further embodiments, the structure identification unit 24 may identify an anomaly in the patient, for example a missing organ. In some embodiments, the structure identification unit 24 may determine the presence of a medical condition.

The metadata unit may validate (or populate) metadata based on the determined at least one property of the patient. Validating (or populating) metadata based on a determined property may include determining whether the metadata is consistent with the determined property.

For example, in some embodiments the metadata (for example, DICOM data elements) includes data related to orientation for example Patient Position (0018, 5100). Patient Position specifies the position of the patient relative to the imaging equipment space, for example whether the patient is scanned feet first or head first and whether the patient is prone or supine. The structure identification unit 24 determines an orientation based on the identified anatomical structures. The metadata unit 26 then performs a consistency test on the determined orientation and the orientation in the Patient Position data element. If the determined orientation and the orientation in the Patient Position data element are consistent, no further action is taken. If there is a discrepancy between the determined orientation and the value in the Patient Position data element, a warning message is displayed to the user, a flag is added to the file, or any other appropriate action is taken. In other embodiments, Patient Orientation Code Sequence (0054, 0410) may be verified or populated. Verification of orientation may be relevant in the detection of possible left right inversion errors.

In other embodiments, the metadata includes DICOM data elements corresponding to Image Orientation Patient (0020, 0037). Image Orientation Patient (0020, 0037) is the mandatory attribute that describes orientation. In further embodiments the metadata includes DICOM data elements corresponding to View Code Sequence (0054, 0220) which allows other components of the view orientation to be specified, such as alignment with cardiac axes.

In another embodiment, the patient sex identified by the structure identification unit 24 may be used to validate or populate the DICOM data element corresponding to Patient Sex (0010, 0040). The identified patient sex may be compared with the contents of the Patient Sex data element and any discrepancies highlighted.

Any property determined by the structure identification unit 24 may be used in validation of any appropriate metadata. The property determined by the structure identification unit and the property of the metadata with which it is compared may be different properties. For example, in one embodiment, the metadata unit 26 compares the sex determined by the structure identification unit 24 to the medical condition indicated in the metadata. In one example, the structure identification unit 24 identifies that the patient is female, while a DICOM data element indicates that the patient has a disorder that is usually only present in men. The metadata unit 26 determines that there is an inconsistency between the property and the metadata, and warning message is generated.

The process of FIG. 3 may be used to validate or populate other forms of metadata, for example metadata associated with different types of file other than DICOM, attributes that are not standard DICOM attributes, or additional files that are associated with image data sets 40. Metadata may include tags, labels, records, files or any other suitable form of data that is additional to the image data and may be associated with the image data. Metadata may include metadata in proprietary or semi-proprietary formats such as MINT (medical imaging network transport), Findings or Snapshots.

In some embodiments, the process of FIG. 3 may be used to create appropriate XDS metadata information in a device creating XDS entries or to validate existing XDS metadata information.

In some embodiments, the process of FIG. 3 may be used to validate or populate anatomic information in HL7 clinical data. For example, HL7 CDA (Clinical Document Architecture) documents encoding imaging results may include anatomic information that is based on a DICOM study. HL7 FHIR (Fast Healthcare Interoperability Resources) Imaging Study resources contain a summary of a DICOM study, including anatomic information.

In the above embodiments, metadata associated with an image data set 40 is validated by comparison to the image data set 40 itself, by registering the image data set 40 to a virtual anatomy. In further embodiments, the validated metadata may further be compared to additional data, for example data in a patient's file or details of the requested scan.

The list of anatomical structures that is identified in the image data set 40 may be compared to additional data in some embodiments, for example data in a patient's file or details of the requested scan. In one embodiment, the list of anatomical structures is compared against the body part that was requested. A message or report is generated detailing any discrepancies between the body part originally requested, and the anatomical structures identified in the image data set 40.

In the above embodiments, the image data set 40 is registered with a virtual anatomy by using landmarks. In other embodiments, any other method of registration may be used. The registration may be rigid, affine, or non-rigid, for example free-form.

In each of the embodiments above, image data is registered to a mesh-based virtual anatomy by using anatomical landmarks to establish a mapping between the data sets. In further embodiments, image data may be registered to a volumetric virtual anatomy, for example by using image-based registration. However, image-based registration may be more computationally intensive, hence slower, than mapping between landmarks. In other embodiments, the virtual anatomy may comprise only a set of bounding boxes. In alternative embodiments, the image data set 40 may be registered to any appropriate further data set. For example, an atlas based on real patient data may be used instead of a virtual anatomy.

Using landmarks may provide a relatively quick, computationally efficient method of registering patient data and mesh-based virtual anatomy data. Only a relatively small number of points in each data set (for example 127 or fewer points in above embodiments) is required to be identified and located. The registration of images using landmarks may be performed using known methods. Anatomical landmarks may be clearly defined anatomically, such that the matching of corresponding points in different data sets may be likely to be accurate.

Although the registration of the image data set 40 to a virtual anatomy has been described, in alternative embodiments, the detected landmarks are used to automatically identify structures in the image data set 40 without performing a registration and without reference to virtual anatomy data.

In some such embodiments, the detected landmarks may be used as a tagging mechanism. The structure identification unit 24 detects landmarks in the image data set 40 as described above, for example by using classifiers or any other appropriate landmark detection method. Each landmark has an anatomical definition. For example, in one embodiment, one landmark marks the superior pole of the right kidney and another marks the apex of the right lung.

The structure identification unit 24 uses the anatomical definition of each landmark to identify anatomical structures that are present in the image data set 40. For example, if the landmark marking the superior pole of the right kidney is found to be present in the image data set 40, the structure identification unit 24 identifies that the right kidney is present in the image data set 40. If the landmark marking the apex of the right lung is found to be present in the image data set 40, the structure identification unit 24 identifies that the right lung is present in the image data set 40.

The metadata unit 26 then uses the identified anatomical structures to validate or populate metadata associated with the image data set 40. In some embodiments, the metadata unit 26 performs a consistency test on each image data set 40 and its associated metadata. If each anatomical structure that is identified in the metadata (for example, in the Body Part Examined data element) is consistent with a structure that has been identified using a landmark, then the consistency test is passed. If an anatomical structure identified in the metadata is not consistent with any of the structures that have been identified by landmarks, the consistency test is failed. If the relevant metadata is empty (no anatomical structure is identified in the metadata) then the consistency test is failed.

In some embodiments, the determination of consistency in embodiments that do not use registration is similar to that described above for embodiments using registration. Thus, for example, a first anatomical structure may be considered to be consistent with a second anatomical structure if the first anatomical structure is the same as the second anatomical structure, if the first anatomical structure is part of the second anatomical structure, or if the second anatomical structure is part of the first anatomical structure.

In alternative embodiments, a less rigorous standard of consistency may be applied in embodiments in which anatomical structures are identified by using landmarks directly, and not by using registration. For example, an anatomical structure may be considered to be consistent with a second anatomical structure if the structures are adjacent, or are in the same body region. In some embodiments, the number of landmarks defined within the body (for example, 127 landmarks) may be substantially less than the number of anatomical structures in the body, and a test of consistency that requires structures to be in the same region may be used in such embodiments.

Although in the above embodiments, anatomical structures in the image data set 40 are identified using landmarks, in alternative embodiments any method of identifying anatomical structures may be used. For example, in some embodiments, segmentation may be used in addition to or instead of landmark detection.

In some embodiments, the process of FIG. 3 is used to validate DICOM data elements where a procedure is used that allows multiple examination orders to be performed in a single scan. On or after scanning, separate patient files are automatically created for each requested order. The process of FIG. 3 is then used to confirm that the original data has been divided correctly by identifying anatomical structures in each of the created image data sets 40, and comparing those anatomical structures with the respective DICOM data elements associated with each of the created image data sets 40.

In some embodiments, the process of FIG. 3 is used to assist automatic categorization system. An automatic categorization system may be in use that takes values for DICOM attributes as its input and then stores patient data accordingly. The process of FIG. 3 may be used to check that the DICOM data elements actually reflect the contents of the images and hence avoid mis-categorization.

The validation algorithm outlined above with reference to FIG. 3 may provide an automatic mechanism for validating the contents of a patient's imaging dataset which has been stored using the DICOM standard against the DICOM data elements used to describe it. The process of FIG. 3 analyzes the actual image data to determine the anatomical content, rather than analyzing only supporting clinical data such as linked reports.

Certain embodiments comprise, for images stored in DICOM format, a method of validating the DICOM data elements stored in the DICOM header with the actual contents of the image data. The method comprises automatically identifying anatomical structures within the image data and validating the DICOM data elements against the detected anatomical structures.

The identification of anatomical structures may be performed by automatically detecting anatomical landmarks in the image data, using the anatomical landmarks to register a virtual anatomy with the patient data set, calculating the bounding volume of the patient data set in the virtual anatomy space, and performing intersection tests between the calculated bounding volume and the anatomical structures contained in the virtual anatomy to determine the anatomical structures contained in the patient data set.

The validation of the DICOM data elements may utilize a clinical ontology to help compare the anatomical location of the detected structures and those defined by the DICOM data elements.

Following validation of the DICOM data elements, a warning may be issued if inconsistencies between the image data and data elements are detected.

In some embodiments, the registration of the medical imaging data with the virtual anatomy data comprises a rigid registration. In some embodiments, the registration of the medical imaging data with the virtual anatomy data comprises a non-rigid registration.

Although particular embodiments have been described above, features of any embodiment may be combined with features of any other embodiment.

Although the above embodiments have been described in relation to CT scans of the human body, in other embodiments any medical image of any modality may be used (where medical includes veterinary). For example, image data set 40 may comprise CT, MR, PET, SPECT or ultrasound data.

Although landmarks may each comprise a single point in an image data set 40, for example a single pixel or voxel, it will be understood that in alternative embodiments each landmark may comprise any suitable image data item, for example a larger block of image data representing a region larger than a single pixel or voxel. Other anatomical identifiers may be used instead of landmarks.

In certain embodiments there is provided, for images stored in DICOM format, a method of validating DICOM data elements stored in a DICOM header with actual contents of image data, comprising automatically identifying anatomical structures within the image data and validating the DICOM data elements against the detected anatomical structures. The identification of the anatomical structures may be performed by automatically detecting anatomical landmarks in the image data, using the anatomical landmarks to register a virtual anatomy with the image data, calculating a bounding volume of the image data in the virtual anatomy space, and performing an intersection test between the bounding volume and the anatomical structures contained in the virtual anatomy to determine the structures contained in the image data. The validation of the DICOM data elements may utilize a clinical ontology to help compare the anatomical location of the detected structures and those defined by the DICOM data elements. Following validation of the DICOM data elements a warning may be issued if inconsistencies between the image data and DICOM data elements are detected It will be well understood by persons of ordinary skill of the art that embodiments may implement certain functionality by means of a computer program or computer programs having computer-readable instructions that are executable to perform the method of the embodiments. The computer program functionality could be implemented in hardware (for example by means of CPU). The embodiments may also be implemented by one or more ASICs (application specific integrated circuit) or by a mix of hardware or software.

Whilst particular units have been described herein, in alternative embodiments functionality of one or more of these units can be provided by a single unit, or functionality provided by a single unit can be provided by two or more units or other components in combination. Reference to a single unit encompasses multiple components providing the functionality of that unit, whether or not such components are remote from one another, and reference to multiple units encompasses a single component providing the functionality of those units.

Whilst certain embodiments have been described, these embodiments have been presented by way of example only, and are not intended to limit the scope of the invention.

Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical image data processing apparatus configured to process a medical image data set and metadata associated with the medical image data set, the apparatus comprising:
processing circuitry configured to
automatically identify at least one anatomical structure of the medical image data set, wherein the medical image data set includes volumetric or two-dimensional image data obtained from a scanner and the automatic identifying of the at least one anatomical structure includes processing the volumetric or two-dimensional image data to identify the at least one anatomical structure; and
receive the metadata associated with the medical image data set, identify at least one anatomical structure or region from the metadata, and validate the metadata associated with the medical image data set based on the identified at least one anatomical structure by comparing the at least one anatomical structure identified from the metadata with the at least one anatomical structure identified by processing the volumetric or two-dimensional image data,
wherein the processing circuitry is further configured to at least one of generate an error code, raise an exception, and provide a warning signal when it is determined from the comparing that the anatomical structure or region identified from the metadata is not consistent with the anatomical structure identified by processing the volumetric or two-dimensional image data.

2. The apparatus according to claim 1, wherein at least one anatomical structure or region is identifiable from the metadata, and the processing circuitry is further configured to determine whether the at least one identified anatomical structure of the medical image data set is consistent with the at least one anatomical structure or region identified from the metadata of the medical image data set.

3. The apparatus according to claim 2, wherein the processing circuitry is further configured to determine whether the at least one identified anatomical structure of the medical image data set is consistent with the at least one anatomical structure or region identified from the metadata of the medical image data set by
determining whether the at least one identified anatomical structure of the medical image data set and the at least one anatomical structure or region identified from the metadata are expected to be present in substantially a same region of a human or animal body.

4. The apparatus according to claim 2, wherein the processing circuitry is further configured to determine whether the at least one identified anatomical structure of the medical image data set is consistent with the at least one anatomical structure or region identified from the metadata with reference to anatomical ontology data.

5. The apparatus according to claim 1, wherein the processing circuitry is further configured to determine at least one property of a human or animal subject of the medical image data set from the at least one identified anatomical structure, and determine whether the determined at least one property is consistent with at least one property represented by the metadata.

6. The apparatus according to claim 5, wherein the determined at least one property comprises at least one of age, sex, and presence of a medical condition.

7. The apparatus according to claim 1, wherein the processing circuitry is further configured to determine at least one property of the medical image data set, or of a scan used to produce the medical image data set, from the at least one identified anatomical structure, and the processing circuitry is further configured to determine whether the determined at least one property is consistent with at least one property represented by the metadata.

8. The apparatus according to claim 7, wherein the at least one property of the medical image data set, or of the scan used to produce the medical image data set, comprises orientation of a human or animal body that is the subject of the medical image data set, zoom or magnification level, or size of a scan area or volume.

9. The apparatus according to claim 1, wherein the processing circuitry is further configured to obtain a registration of the medical image data set and a further data set that includes or is associated with at least one anatomical identifier.

10. The apparatus according to claim 9, wherein the at least one anatomical identifier comprises at least one anatomical landmark.

11. The apparatus according to claim 10, wherein the processing circuitry is further configured to identify at least one anatomical landmark in the medical image data set, and register the identified at least one anatomical landmark of the medical image data set and the at least one anatomical landmark of the further data set.

12. The apparatus according to claim 9, wherein the further data set comprises a virtual anatomy data set.

13. The apparatus according to claim 9, wherein the processing circuitry is further configured to determine from the registration a region of the further data set that corresponds to an area or volume represented by the medical image data set, and
to perform the automatic identifying of at least one anatomical structure by determining, from the at least one anatomical identifier of the further data set, at least one anatomical structure that falls within the determined region of the further data set.

14. The apparatus according to claim 13, wherein the area or volume of the medical image data set comprises an area or volume bounded by an outer boundary of the medical image data set.

15. The apparatus according to claim 13, wherein the anatomical identifiers comprise or are associated with bounding boxes or other position data, each representing a position of a respective anatomical structure or region, and
the processing circuitry is configured to determine from the anatomical identifiers of the further data set at least one anatomical structure that falls within the determined region of the further data set by determining whether at least one of the bounding boxes or other position data falls within or overlaps the determined region of the further data set.

16. The apparatus according to claim 1, wherein the processing circuitry is further configured to determine whether or not the metadata is consistent with the identified at least one anatomical structure or with at least one property determined from the identified at least one anatomical structure.

17. The apparatus according to claim 16, wherein the processing circuitry is further configured to generate the error code or raise the exception when it is determined that the metadata is not consistent with the identified at least one anatomical structure or with at least one property determined from the identified at least one anatomical structure.

18. The apparatus according to claim 16, wherein the processing circuitry is further configured to provide the warning signal when it is determined that the metadata is not consistent with the identified at least one anatomical structure or with at least one property determined from the identified at least one anatomical structure.

19. The apparatus according to claim 1, wherein the processing circuitry is further configured to populate the metadata associated with the medical image data set by entering or overwriting data in respect of at least one metadata item.

20. The apparatus according to claim 19, wherein the data comprises an anatomical identifier, or at least one property of a human or animal subject or of the medical image data set determined from the identified at least one anatomical structure.

21. The apparatus according to claim 1, wherein the metadata comprises at least one DICOM data element.

22. The apparatus according to claim 21, wherein the at least one DICOM data element comprises at least one of Body Part Examined (0008, 0015), Anatomic Structure (0008, 2208), and Anatomic Region Sequence (0008, 2218).

23. The apparatus according to claim 1, which comprises or forms part of a Picture Archiving and Communication System (PACS) or Report System.

24. A medical image data processing method to process a medical image data set and metadata associated with the medical image data set, comprising:
    automatically identifying at least one anatomical structure of the medical image data set, wherein the medical image data set includes volumetric or two-dimensional image data obtained from a scanner and the automatic identifying of the at least one anatomical structure includes processing the volumetric or two-dimensional image data to identify the at least one anatomical structure; and
    receiving the metadata associated with the medical image data set;
    identifying at least one anatomical structure or region from the metadata; and
    validating the metadata associated with the medical image data set based on the identified at least one anatomical structure by comparing the at least one anatomical structure identified from the metadata with the at least one anatomical structure identified by processing the volumetric or two-dimensional image data,
    wherein the method further includes at least one of generating an error code, raising an exception, and providing a warning signal when it is determined from the comparing that the anatomical structure or region identified from the metadata is not consistent with the anatomical structure identified by processing the volumetric or two-dimensional image data.

25. A non-transitory computer-readable storage medium storing a computer program comprising computer-readable instructions that are executable to perform a method to process a medical image data set and metadata associated with the medical image data set, comprising:
    automatically identifying at least one anatomical structure of the medical image data set, wherein the medical image data set includes volumetric or two-dimensional image data obtained from a scanner and the automatic identifying of the at least one anatomical structure includes processing the volumetric or two-dimensional image data to identify the at least one anatomical structure; and
    receiving the metadata associated with the medical image data set;
    identifying at least one anatomical structure or region from the metadata; and
    validating the metadata associated with the medical image data set based on the identified at least one anatomical structure by comparing the at least one anatomical structure identified from the metadata with the at least one anatomical structure identified by processing the volumetric or two-dimensional image data,
    wherein the method further includes at least one of generating an error code, raising an exception, and providing a warning signal when it is determined from the comparing that the anatomical structure or region identified from the metadata is not consistent with the anatomical structure identified by processing the volumetric or two-dimensional image data.

* * * * *